US006472662B1

United States Patent
Archie

(10) Patent No.: US 6,472,662 B1
(45) Date of Patent: Oct. 29, 2002

(54) AUTOMATED METHOD FOR DETERMINING SEVERAL CRITICAL DIMENSION PROPERTIES FROM SCANNING ELECTRON MICROSCOPE BY USING SEVERAL TILTED BEAM OR SAMPLE SCANS

(75) Inventor: Charles Neill Archie, Granite Springs, NY (US)

(73) Assignee: International Business Machines Corporation, Armonk, NY (US)

( * ) Notice: Subject to any disclaimer, the term of this patent is extended or adjusted under 35 U.S.C. 154(b) by 17 days.

(21) Appl. No.: 09/651,993

(22) Filed: Aug. 30, 2000

(51) Int. Cl.[7] ............................................. G01N 23/225
(52) U.S. Cl. ................. 250/307; 250/306; 250/252.112
(58) Field of Search ................................. 250/307, 310, 250/252.1 R, 306, 311, 252 R, 442.11

(56) References Cited

U.S. PATENT DOCUMENTS

| | | | | |
|---|---|---|---|---|
| 4,733,074 A | * | 3/1988 | Kato et al. ................... | 250/307 |
| 5,869,833 A | | 2/1999 | Richardson et al. ......... | 250/310 |
| 5,969,273 A | | 10/1999 | Archie et al. ............... | 73/865.8 |
| 6,025,600 A | | 2/2000 | Archie et al. ............ | 250/396 R |
| 6,054,710 A | * | 4/2000 | Bruggeman ................. | 250/307 |
| 6,066,849 A | | 5/2000 | Masnaghetti et al. ....... | 250/310 |
| 6,114,695 A | * | 9/2000 | Todokoro et al. ........... | 250/310 |

OTHER PUBLICATIONS

"Sidewall angle measurment using CD SEM", Su et al, IEEE/SEMI, 1998, pp. 259–261.*
Charles Archie, Jerry Lowney and Michael T. Postek, "Modeling and Experimental Aspects of Apparent Beam Width as an Edge Resolution Measure", SPIE Conference on Metrology, Inspection and Process Control for Microlithography XIII, SPIE, vol. 3677, pp. 669–685 (Mar. 1999).

* cited by examiner

Primary Examiner—Jack Berman
Assistant Examiner—K Fernandez
(74) Attorney, Agent, or Firm—Graham S. Jones, II; H. Daniel Schnurmann

(57) ABSTRACT

To obtain data pertaining to the surface characteristics of a sample, a control method adjusts a tilted rastered E-beam to in SEM to a first/next tilt condition and navigates the SEM-beam to a sample site. The system performs a fine alignment step. Then the system scans a region of a sample to acquire a waveform. The system analyzes the waveform to determine the DESL value for each edge of interest. The system tests whether there is sufficient information available for each structural edge. If NO, the system repeats the above steps starting by changing the value of the tilt angle to acquire another waveform. If YES, the system determines the height and sidewall angles for each structural edge. Then the system reports the sidewall angle and the structure height for each edge of the structure under test. The system then corrects the critical dimension measurement determined from 0 degrees tilt scanning.

17 Claims, 12 Drawing Sheets

AUTOMATED METHOD FOR DETERMINING SEVERAL CRITICAL DIMENSION PROPERTIES FROM SCANNING ELECTRON MICROSCOPE BY USING SEVERAL TILTED BEAM OR SAMPLE SCANS

BACKGROUND OF THE INVENTION

1. Field of the Invention

This invention relates to methods and apparatus for determining the critical dimension of workpieces. 2. Description of Related Art An occasional problem with a conventional automated Critical Dimension Scanning Electron Microscope (CD SEM) measurement is poor correlation thereof with subsequent electrical measurements. This problem can be due to feature positions to be measured, for example, the foot of a photoresist line being obscured by an overhanging structure. Other examples are T-topping, undercutting, and negative angle or recursive sidewall.

Currently available standard top/down CD SEM systems prevent the SEM electron beam (SEM-beam) from tilting relative to the sample for several reasons. However, at least one CD SEM provider is developing a system that can quickly and automatically tilt the beam by several degrees and acquire secondary electron waveforms or images from scanning the same structure at various tilt angles.

Such technology can advance the core capability of the CD SEM only if the additional information resulting from changing the angle of deflection of the scanning SEM-beam can be used quickly and in an automated fashion to improve the accuracy of measurement. Problems needing to be solved include positional alignment of the waveforms, separating various contributors to the effective edge width of a tilted structure, and finally, synthesizing the information into a critical dimension measurement.

There has been considerable effort directed at extracting three-dimensional information from two images acquired at different angles of view (stereoscopic imaging), as in robotic vision.

These methods use the phenomena of shadowing and parallax to calculate the relative coordinates (including height) of identifiable features in two or more images. Unfortunately, on the scale of interest for CD metrology (nanometers) and for the primary structures of interest (straight lines or spaces), there are few dependable identifiable features. More seriously, the SEM-beam interaction with the structure is very different from the interaction physics of these other applications. Successful sidewall metrology needs to account for the finite size of the SEM-beam and the interaction volume within the structure material.

An example of scatterometry is found in the area of semiconductor manufacturing metrology. In the approach recently commercialized by Biorad, a defocussed laser beam scatters off of a periodic array of structures on the wafer (target) and the zeroth order diffracted beam intensity is measured for two polarizations of light. Data is collected as a function of the incident angle. The resulting waveform is compared with simulations. The ability and resources for calculating the electromagnetic response for model structures is crucial to this approach. Other variations on this approach include using higher order diffracted beams or multiple wavelengths of light. None of these methods deals with images or waveforms acquired by scanning focused SEM-beams or the very different interaction physics of an SEM-beam with matter.

One noteworthy approach to improving the accuracy of top/down CD SEM metrology is the work of the Spectel Corporation. System responses, based on the use of an approximate simulation of the SEM-beam interaction with model structures, produce a database of waveforms. The best match to the actual waveform is used to interpret the measurement. That is similar in concept to the commercialized scatterometry approach. Possibly, this approach can be applied to the tilted SEM-beam CD SEM system. However, the overhead in calculation resources is significant and the accuracy of the modeling, especially in the presence of sample charging, is highly questionable.

Beam tilting is the same thing as beam deflection that are used for column alignment as exemplified by U.S. Pat. No. 6,066,849 of Masnaghetti et al. for "Scanning Electron Beam Microscope" which applies an x tilt voltage and a y tilt voltage but as described at Col. 11, lines 41–53 , it is employed as follows:

"The upper quadrupole . . . is configured to align the beam after a particular gun lens voltage is selected. In other words, the beam may have to be moved such that it is realigned with respect to the aperture. This realignment is accomplished by supplying an X and Y tilt voltage from the multiplexer control system . . . and the beam may be realigned with respect to the aperture by setting the X and Y tilt voltage values that are supplied to the upper quadrupole . . . "

See U.S. Pat. No. 5,969,273 of Archie et al. "Method and Apparatus for Critical Dimension and Tool Resolution Determination Using Edge Width" describes measuring hump width to obtain SEM resolution information. See U.S. Pat. No. 6,025,600 of Archie et al. "Method for Astigmatism Correction in Charged Particle Beam Systems"; and U.S. Pat. No. 5,869,833 of Richardson et al. "Electron Beam Dose Control for Scanning Electron Microscopy and Critical Dimension Measurement Instruments".

A common prior art algorithm is to declare the outer extremal slope location for each edge of a feature on a sample to be the location of the edge and therefore to report the distance between these locations.

SUMMARY OF THE INVENTION

| Glossary | | |
|---|---|---|
| DESL | = | Distance between Extremal Slope Locations in SEM data for a single edge of a feature |
| Extremal Slope | = | Maximum or minimum slope or rate of change of a function |
| Height | = | Height of structural edge of a feature on a sample |
| Interaction volume | = | Extent within a sample of excited electron activity due to the electron beam of the microscope |
| $K_0$ | = | constant determined during calibration |
| K | = | constant determined during calibration |
| Threshold value | = | Empirically determined minimum of valid DESL value |
| Waveform | = | One-dimensional digitized line scan |
| $\theta$ | = | Relative angle between SEM-beam direction and sidewall |

The discovery of a simple relationship between structure properties and the Distance between Extremal Slope Locations (DESL) in SEM data as a function of electron beam tilt angle forms the basis for an automated methodology of obtaining such structural properties without the need for extraordinary alignment or 3D (three-dimensional) reconstruction techniques. Normally careful alignment of the data is required to extract three-dimensional information from multiple SEM images or waveforms (one-dimensional digitized line scans). In cases of interest, related to this invention, that alignment is on the nanometer scale. Today, it is not possible to acquire multiple SEM images or waveforms on the nanometer scale, after stage movement, with blind navigation. Use of pattern recognition can improve matters, if suitable pattern recognition targets that are required are available, which is generally not true.

This invention gets around the alignment problem by not requiring alignment. Instead, each waveform (either directly obtained from the SEM or extracted from a SEM image) can be analyzed to find the locations of extremal slopes for each structural edge of interest. The DESL value so determined should have a precision of a few nanometers. With calibration, the accuracy of the DESL value measured should be comparable to its precision.

In order to automate a fast determination of structure properties (height as well as, left and right sidewall angles), the method of this invention minimizes the actual number of measurements in real time by requiring that for each feature edge, there are two DESL values determined at different tilt angles that are larger than a threshold value, which is set at the time of calibration.

Variations of this include requiring only one DESL measurement greater than the threshold value if either sidewall angle or structure height is already know. Another variation is to use the height determined from one edge analysis in the analysis for the other edge. This then requires two DESL measurements above the threshold value for one side but only one DESL measurement above the threshold value for the other side. Another variation, is to allow the gathering of additional DESL information beyond the minimum necessary in order to improve measurement uncertainty or to perform consistency checking.

The analysis of the DESL information as a function of tilt angle is as follows: Provided all the DESL values being used for one edge (two or more) are greater than the threshold value, then the DESL values [nm] versus tilt angle [radians] are fitted to a straight line. The important properties of the straight line are the slope and the Y-axis intercept. Because the cases of practical interest have the sidewall angle and the beam tilt angles small (less than 10 degrees), tan θ=θ is a good approximation. If applied to a situation with larger angles, the modification of the method is straightforward. In the small angle case, the slope determined from the straight-line-fit is the structure height in nanometers. The Y-axis intercept determined from the linear regression determines the sidewall angle by the following formula:

In a situation where one of the DESL values to be used is close to the value of the sum of $K_0+K$ determined during calibration, then a more accurate, non-linear analysis is necessary. The DESL and tilt angle values will be fit to the following functional form with the structure height H and sidewall angle SA being the fitting parameters:

$$DESL = \sqrt{[H*\tan(\phi_0 + \varphi_e)]^2 + K_0^2} + K$$

where
$H$ = structure height,
$\phi_0$ = sidewall angle deviation from vertical,
$\varphi_e$ = tilt of the SEM-beam,
$DESL$ = Distance between Extermal Slope Locations
$K_0$ = constant determined during calibration
$K$ = constant determined during calibration Once the structural properties of height H and left and right sidewall angles LSA and RSA are determined, these can be used to determine a more accurate value for the Critical Dimension of the structure. Often times the structure being measured is made of photoresist patterned by lithography. This photoresist pattern will be used in a subsequent processing step as a mask. For processes like isotropic etching, ion diffusion, and plating, the base width of the structure defines the extent of this subsequent processing step and therefore is the Critical Dimension needing to be measured. So in cases such as these and more, the measurement of greatest value is the structure Base Width BW. In other cases, such as a subsequent anisotropic processing step, the Maximum Structure Width MSW anywhere from structure top to base is most important. There is a need for flexibility in the use of the additional structural properties of height H and sidewall angle SA since the critical dimension CD depends not only on the actual structure but upon the application of this structure to a subsequent processing step.

In the case where the Base Width is the Critical Dimension, prior art algorithms which only use untilted electron beam information, are usually adequate provided the base is not obscured because of a Negative Sidewall Angle. As stated above a common prior art algorithm is to declare the outer extremal slope location for each edge to be the location of the edge and therefore report the distance between these locations without taking into account that one or both the edges of the structure may be obscured by a tilted Negative Sidewall Angle with the corner above the edge obscuring the sidewall and the feature to be detected. Therefore, the first use of the new information is to confirm or deny the applicability of the prior art algorithm. If either sidewall has a Negative Sidewall Angle, then either a correction must be made to the prior art algorithm result or a totally new algorithm which uses all the structural information should be used. While this decision making and calculation could be made by a host computer once all the information has been sent from the CDSEM, it is preferred for real time reporting that the CDSEM computer actually do this processing.

Assuming that the prior art algorithm in the case of a negative sidewall angle is actually finding the location of the edge only at the top of the structure, then the correction that must be added to correctly determine the edge base location is H tan(SA) where H is the structure height and SA the sidewall angle. This correction should be applied to both edges if both have negative sidewall angles. So in general, if CD stands for the Critical Dimension to be reported and CDO stands for the result from the prior art algorithm, then perform the calculations as follows:

| | |
|---|---|
| CD = CD0 | if RSA ≧ 0 and LSA ≧ 0 |
| CD = CD0 + Htan(RSA) | if RSA < 0 and LSA ≧ 0 |
| CD = CD0 + Htan(LSA) | if RSA ≧ 0 and LSA < 0 |
| CD = CD0 + Htan(RSA) + Htan(LSA) | if RSA < 0 and LSA < 0. |

The flexibility needed to handle multiple prior art algorithms and multiple definitions of the critical dimension can be achieved by allowing the user to choose an appropriate value for the constant $K_2$ in the following modified version of the calculation:

| | |
|---|---|
| CD = CD0 | if RSA ≧ 0 and LSA ≧ 0 |
| CD = CD0 + $K_2$Htan(RSA) | if RSA < 0 and LSA ≧ 0 |
| CD = CD0 + $K_2$Htan(LSA) | if RSA ≧ 0 and LSA < 0 |
| CD = CD0 + $K_2$Htan(RSA) + $K_2$Htan(LSA) | if RSA < 0 and LSA < 0 |

In accordance with this invention, a method/system/apparatus for making Scanning Electron Microscope (SEM) scans of a workpiece comprises:

(a) a method/means for setting an SEM beam to a first/next deflection tilt angle, (b) a method/means for scanning of a region of the workpiece at the deflection tilt angle to acquire a waveform, (c) a method/means for analyzing a waveform to determine a DESL value for each edge of interest, (d) a method/means for determining whether there is sufficient information for each structural edge and if NO returning to step (a) and if YES proceeding to step (e), (e) a method/means for determining height and sidewall angle values for each structural edge, and (f) a method/means for reporting the height and sidewall angle for each structural edge.

BRIEF DESCRIPTION OF THE DRAWINGS

The foregoing and other aspects and advantages of this invention are explained and described below with reference to the accompanying drawings in which.

DETAILED DESCRIPTION OF THE PREFERRED EMBODIMENT

Figure 1A:
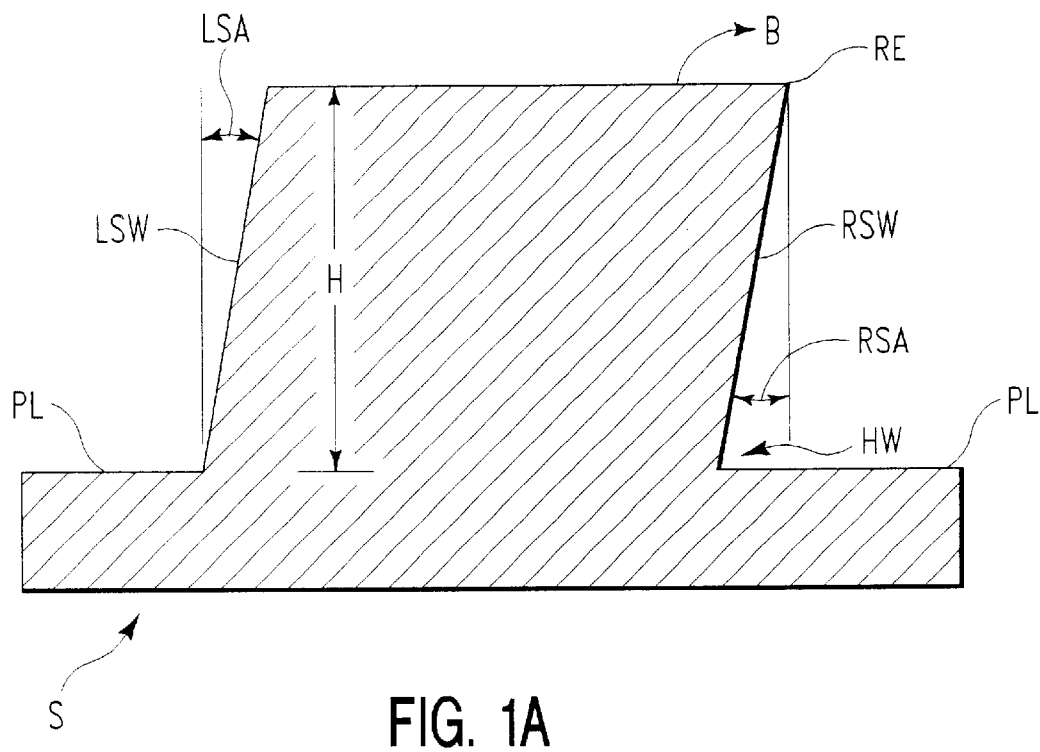
FIG. 1A shows a schematic, cross-sectional, elevational view of an example of a bump formed on a sample.

FIG. 1A shows a schematic, cross-sectional, elevational view of an example of a bump B formed on a sample S. Bump B has a Height (H). The data used to create the graph of FIG. 1B was acquired by simulating a top/down SEM-beam scan of sample S and bump B viewing of FIG. 1A. As seen in FIG. 1A, bump B has an exposed left sidewall LSW at a left sidewall angle LSA which according to a convention of vertical being 0° has a value greater than 0°. The bump B also has a right sidewall RSW with a right sidewall angle RSA less than 0°. Thus the right edge RE of bump B overhangs the right sidewall RSW obscuring both the right sidewall RSW and the "hollow" at the bottom of right sidewall RSW. The large peak LP on the left is aligned with the left edge LE and the small peak SP on the right is aligned with the right edge RE. Manifestly, the acute angle overhang of the right sidewall RSW makes it difficult for a conventional vertical SEM scan to detect the surface of the sample S at the bottom of hollow HW.

Figure 1B:
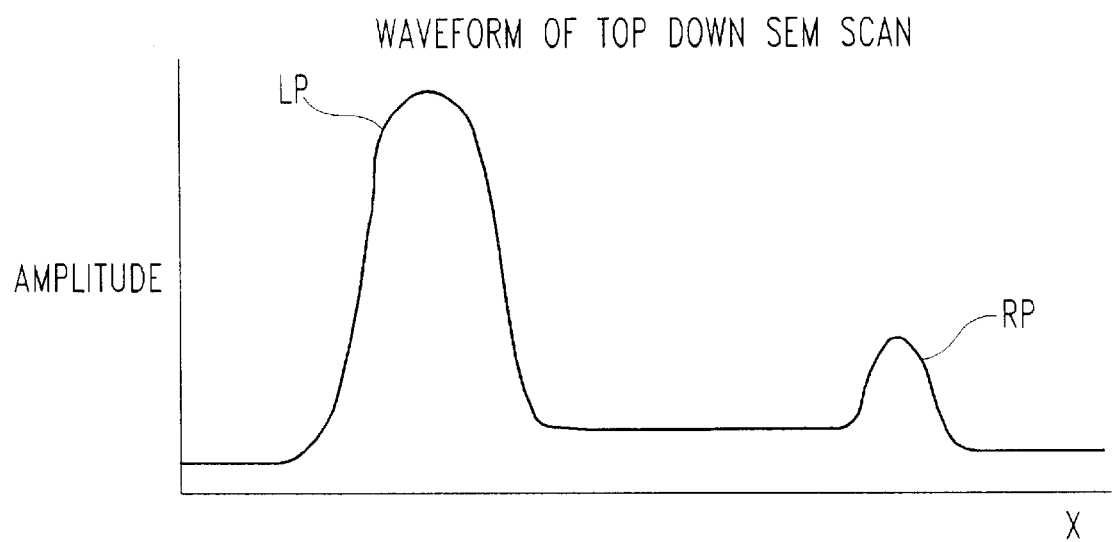
FIG. 1B shows a graph of amplitude vs. distance of an asymmetric SEM waveform provided by a vertical scan of the bump on the sample of FIG. 1A with a conventional SEM-beam with a large peak on the left and a small peak on the right.

FIG. 1B shows a graph of amplitude (proportional to the secondary electron yield) vs. distance X of an asymmetric SEM waveform provided by a vertical scan with a conventional SEM-beam of the sample of FIG. 1A with a large peak LP on the left and a small peak SP on the right.

Figure 2:
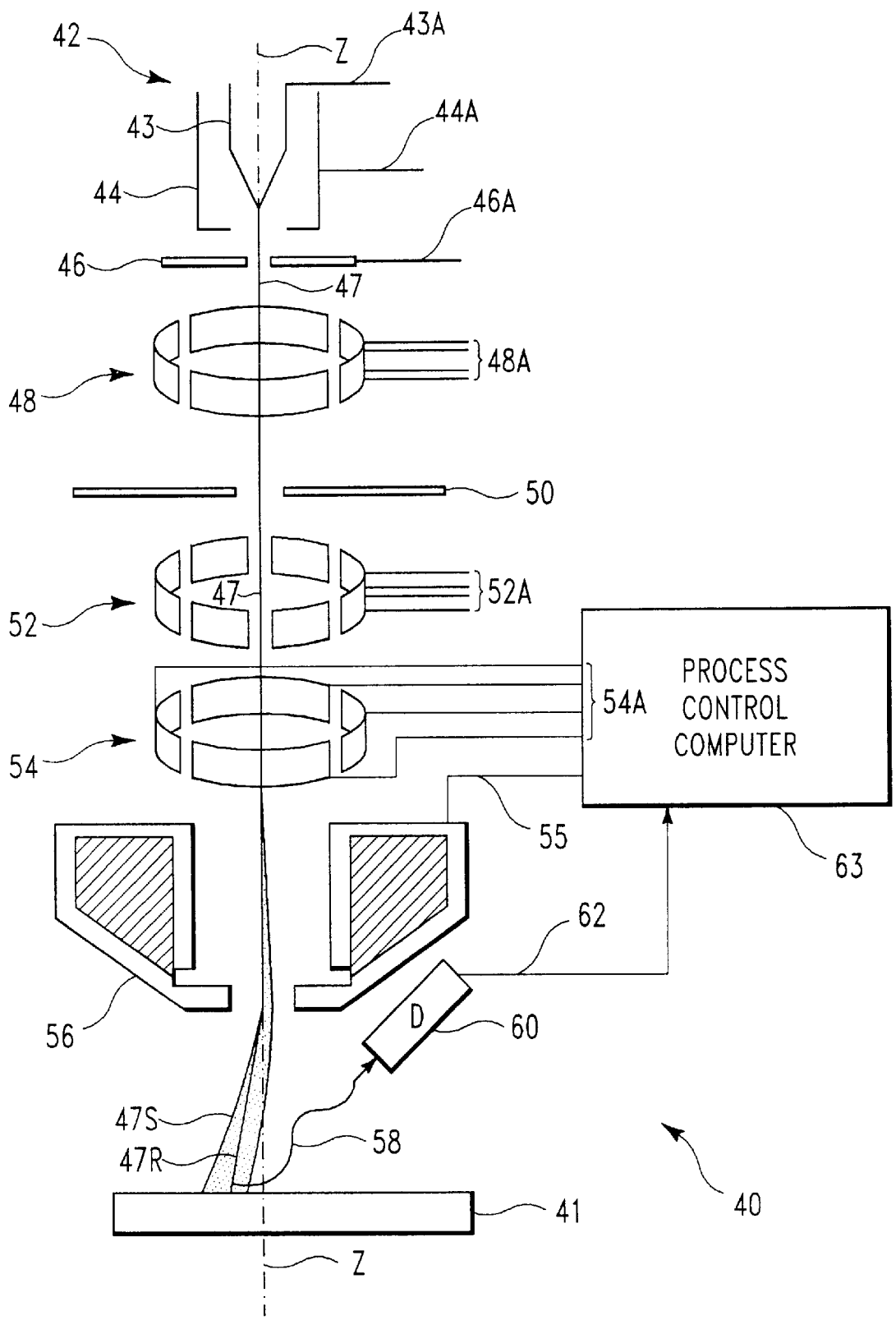
FIG. 2 shows the combination of a workpiece, an SEM system which produces an SEM beam and detects electrons indicating the profile of the workpiece, and a process control computer which all comprise an embodiment of a system adapted to perform the method of this invention on structures such as the bump of FIGS. 1A.

FIG. 2 shows an SEM system 40, a workpiece 41 and a process control computer 63. The SEM system 40 includes an electron gun assembly 42 which includes an SEM-beam source 43, a suppressor 44 open at the bottom and an extractor 46 which generate beam 47 of electrons which are accelerated towards workpiece 41 as will be well understood by those skilled in the art. The SEM-beam source 43 (which may be a thermally assisted tunneling gun) is connected to a power source by cable 43A; the suppressor is connected to a negative voltage by cable 44A; and the extractor 46 is connected to a positive voltage by cable 46A, as will be well understood by those skilled in the art. The beam 47 passes from the electron gun assembly 42 through alignment plates 48 (connected to lines 48A), through aperture 50, and through astigmatism correctors 52 (connected to lines 52A).

The beam 47 then passes through x-y deflecting plates 54 which are connected by a set of lines 54A to a process control computer 63 which provides both tilting of the beam and raster scans of the beam 47 across the sample 41, as will be explained in further detail below. The beam 47 then passes through a magnetic objective lens 56. The result is that a rastered, tilted, lower portion of beam 47 comprising a tilted SEM-beam 47R with a deflection tilt angle is produced scanning across the workpiece 41 as indicated by the scan region 47S (shaded region with the deflection beam tilt angle) on either side of the rastered lower SEM-beam 47R. The scanning, tilted SEM-beam 47R is scanned by the x-y deflecting plates 54 and it should be noted that the tilted, scanned region 47S is shown tilted to the left of the vertical axis Z. The tilt of the SEM-beam 47R is accomplished by providing a bias in the form of a constant voltage added to a scanning sawtooth waveform thereby biasing the voltage to the x-y deflecting plates 54. The bias of the shaded, tilted scan region 47S provides the tilt to the tilted SEM-beam 47R which is able to reach below the edge RE along right sidewall RSW in FIG. 1A down to the surfaces below the hollow HW. The tilted SEM-beam 47R can reach around the corner RE in FIG. 1A down to the bottom of the bump B into the hollow HW. It will be well understood by those skilled in the art that electromagnetic deflection elements may be substituted for the electrostatic deflection elements 48, 52 and 54 in FIG. 2.

Figure 3:
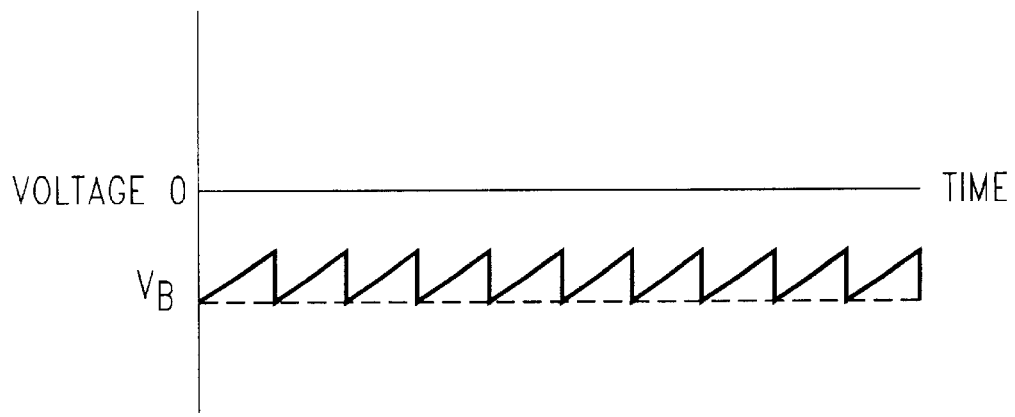
FIG. 3 shows the biased sawtooth waveform applied in FIG. 2 by the process control computer to the line which provides a tilted raster scan of the SEM-beam.

FIG. 3 shows the biased sawtooth waveform applied in FIG. 2 by process control computer 63 to the lines 54A which provides the tilted raster scan of SEM-beam 47R. The biased sawtooth waveform of FIG. 3 has a negative bias voltage $V_B$, so as the sawtooth voltage varies as a function of time, it energizes the x-axis deflection plates 54 to scan the tilted SEM-beam 47R back and forth to the left and the right within the shaded, tilted scan region 47S, but centered to the left of the Z axis in FIG. 2. Over time the value of the bias $V_B$ can be changed so that different angles of tilt can be applied. After such a change the supporting stage upon which the sample 41 rests must move the sample 41 to bring the desired feature such as the bump beneath the scanned beam 47R. The solution of this invention, which is founded on insights gained from SEM-beam modeling work and experiments, identifies key features in the waveforms. Tracking of these features as a function of a deflection tilt angle applied to an SEM-beam provides information that can be interpreted in terms of structure height, sidewall angle, possible obscuration, and critical dimension (CD). Measurements at a minimum of two tilt angles per edge are necessary but the degrees of calculation is modest, i.e., comparable to that of algorithms in use today on top/down CD SEMs.

In the case of substitution of electromagnetic deflection apparatus for the electrostatic deflection elements 48, 52 and 54 in FIG. 2, a bias current is substituted for the bias voltage for the biased sawtooth waveform deflection for tilting the beam 47R to scan within the shaded, tilted scan region 47S.

Figure 4:
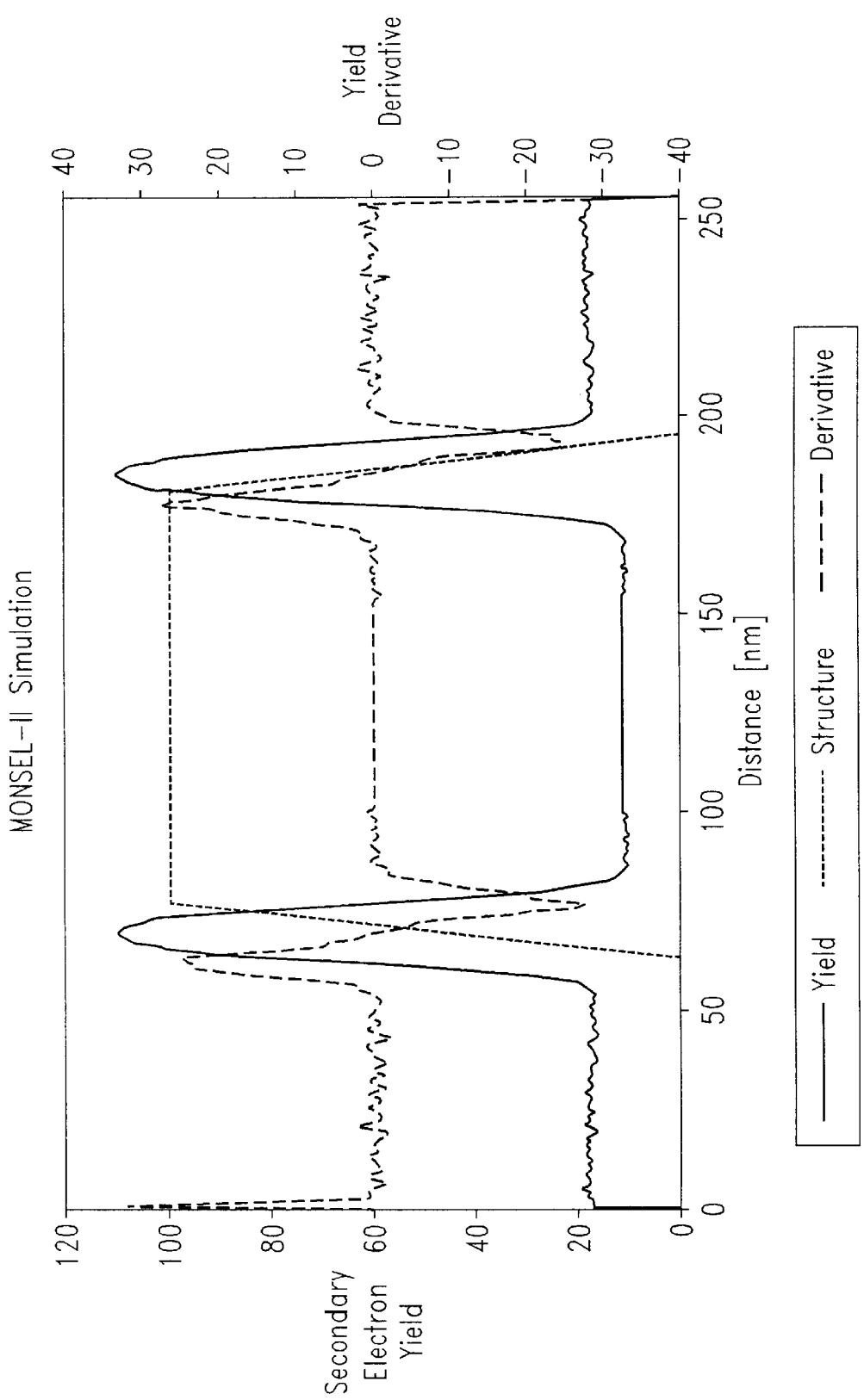
FIG. 4 is a graph as a function of distance in nanometers of a Secondary Electron Yield (SEY) and the first derivative thereof along a one-dimensional scan of an idealized isolated photoresist line formed on a substrate.

Modeling work reported here comes from the use of the Monte Carlo program, MONSEL-II, developed at the National Institute of Standards and Technology (NIST) by J. R. Lowney, "Application of Monte Carlo Simulations to Critical Dimension Metrology in a Scanning Electron Microscope", *Scanning Microscopy*, Vol.10, pp. 667–668 (1996). Also, see C. Archie, J. Lowney and M. T. Postek "Modeling and Experimental Aspects of Apparent Beam Width as an Edge Resolution Measure", *SPIE* vol. 3677, pages 669–685 (1999). FIG. 4 is a graph as a function of distance in nanometers (nm) of a Secondary Electron Yield (SEY) and the first derivative of the SEY along a one-dimensional scan of an idealized isolated resist line (130 nm wide at its base and 800 nm tall) with sidewall angles deviating from vertical by only one degrees (1°). The SEM-beam conditions are a 500 eV landing energy and a 10 nm spot size.

The locations of Extremal (maximum and minimum value) slopes are key measurements for this invention. Each edge has an outer location of an extremal slope and an inner location of an extremal slope. Modeling work indicates that the outer location of an extremal slope is associated with the base of a simple edge structure such as is shown here. The inner location of an extremal slope is associated with the size of the interaction volume. Since the size of the interaction volume depends on both the beam landing energy and the composition of the structure, it is usually not a useful metrology marker. However, the inner location of extreme slope proves to be a very robust invariant when comparing waveforms with different SEM-beam deflection tilt angles.

Figure 5:
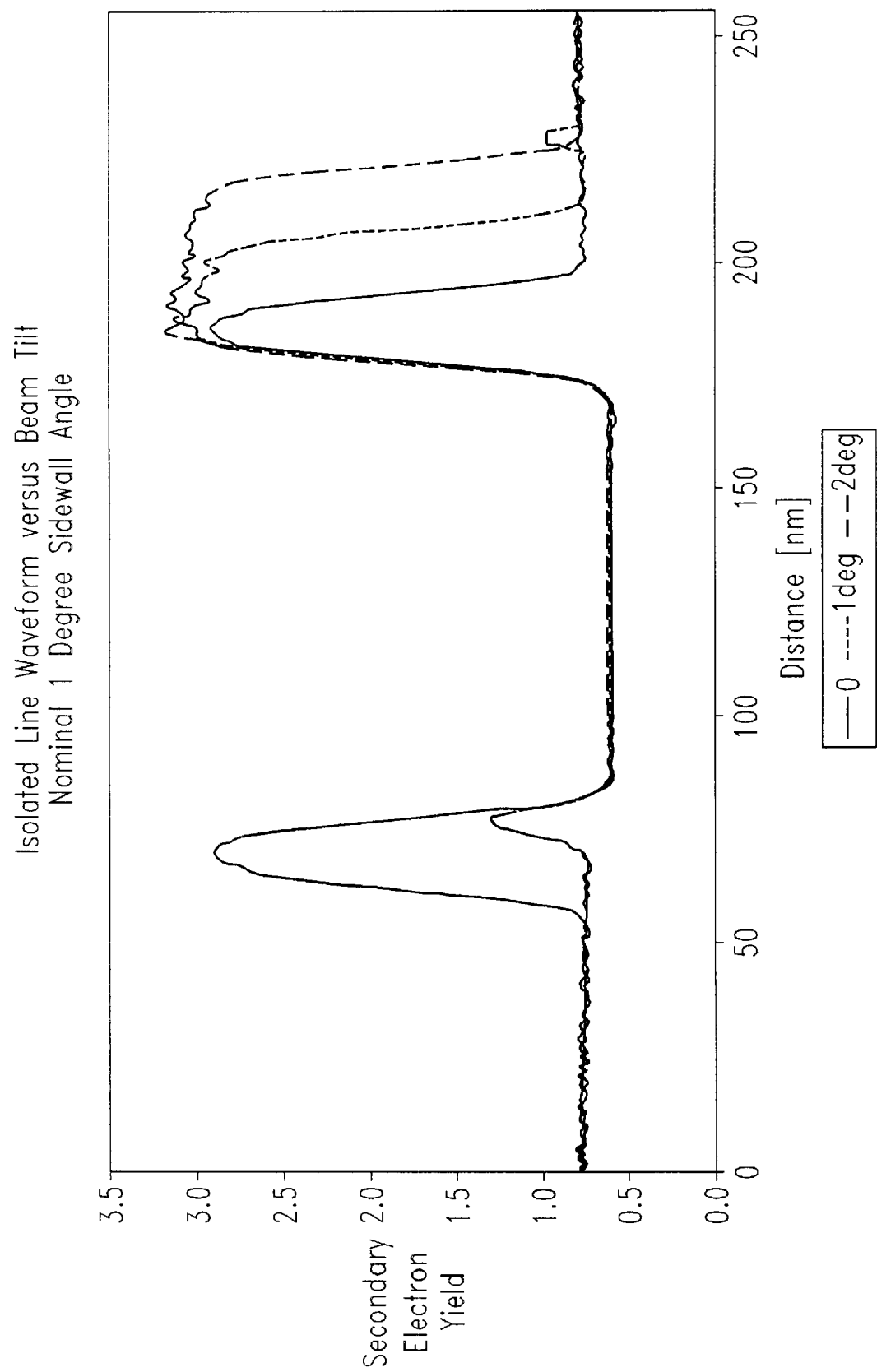
FIG. 5 shows three MONSEL-II derived Isolated Line Waveforms corresponding to tilting the SEM-beam by three different SEM-beam deflection tilt angles.

FIG. 5 shows three MONSEL-II derived Isolated Line Waveforms corresponding to tilting the SEM-beam by three different SEM-beam deflection tilt angles. In FIG. 5 the Isolated Line SEM waveforms corresponding to tilting the SEM-beam deflection angle by three different SEM-beam deflection tilt angles of zero, one and two degrees (0°, 1°, and 2°) for the given structure in FIG. 4. The left sidewall becomes vertical with respect to the SEM-beam at just one degrees (1°) of deflection tilt angle. For two degrees (2°) of SEM-beam deflection tilt angle, the left edge now has an obscured negative angle sidewall and, essentially, the resulting left edge waveform overlays the one degrees (1°) tilt case. The right edge becomes increasingly exposed in going from zero to two degrees (0° to 2°) of tilt.

Figure 6:
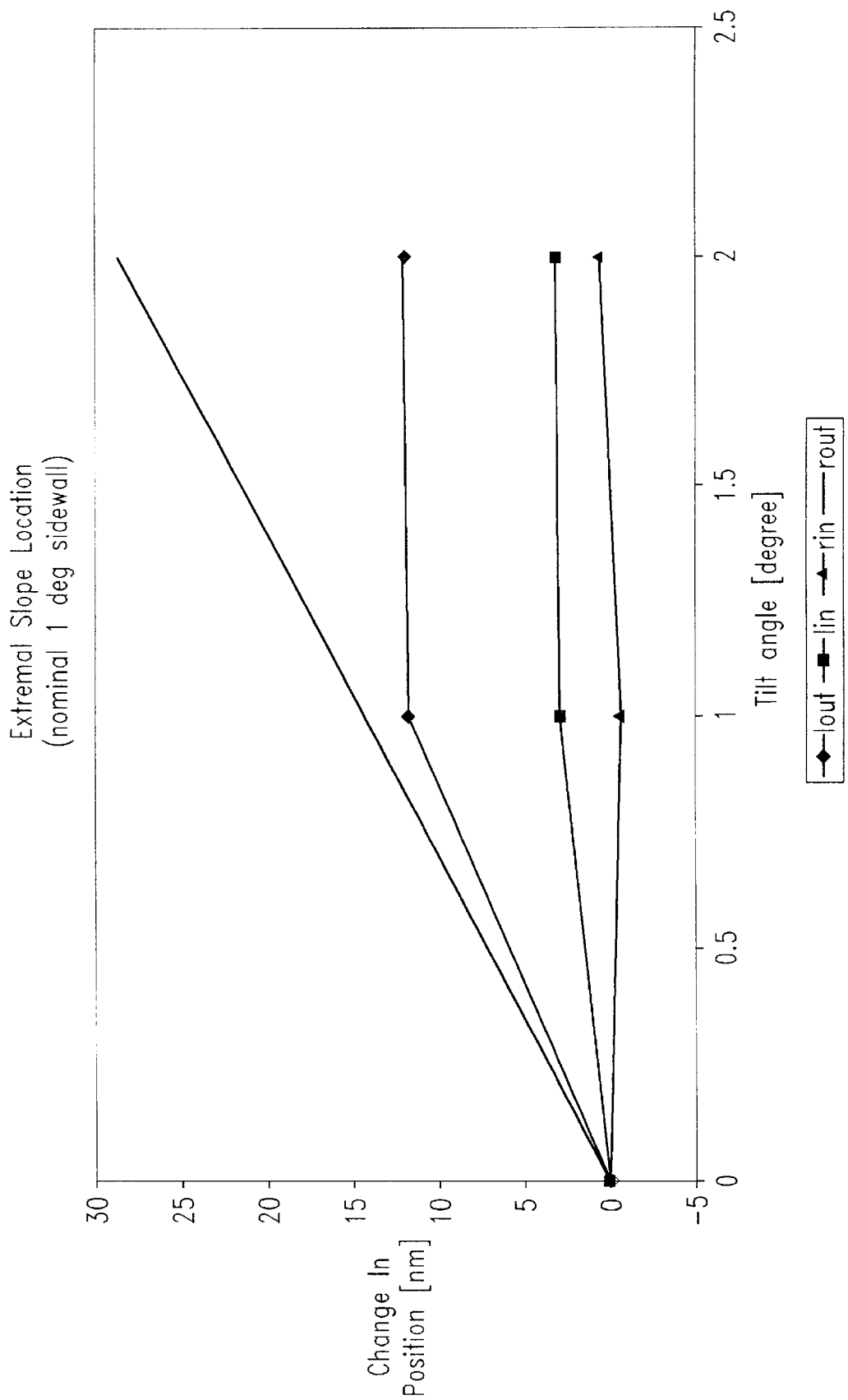
FIG. 6 shows the Extremal Slope Values, i.e. locations of Extremal slopes, versus the SEM-beam deflection tilt angle for waveforms from FIG. 5.

FIG. 6 shows the extremal slope points (nm), i.e. locations of extreme slope values, versus the SEM-beam deflection tilt angle (degrees) for waveforms from FIG. 5, revealing the insensitivity to the tilt at the inner locations of extremal slopes. The outer locations of extremal slope points quantify the changes discussed above with respect to FIG. 5.

Figure 7:
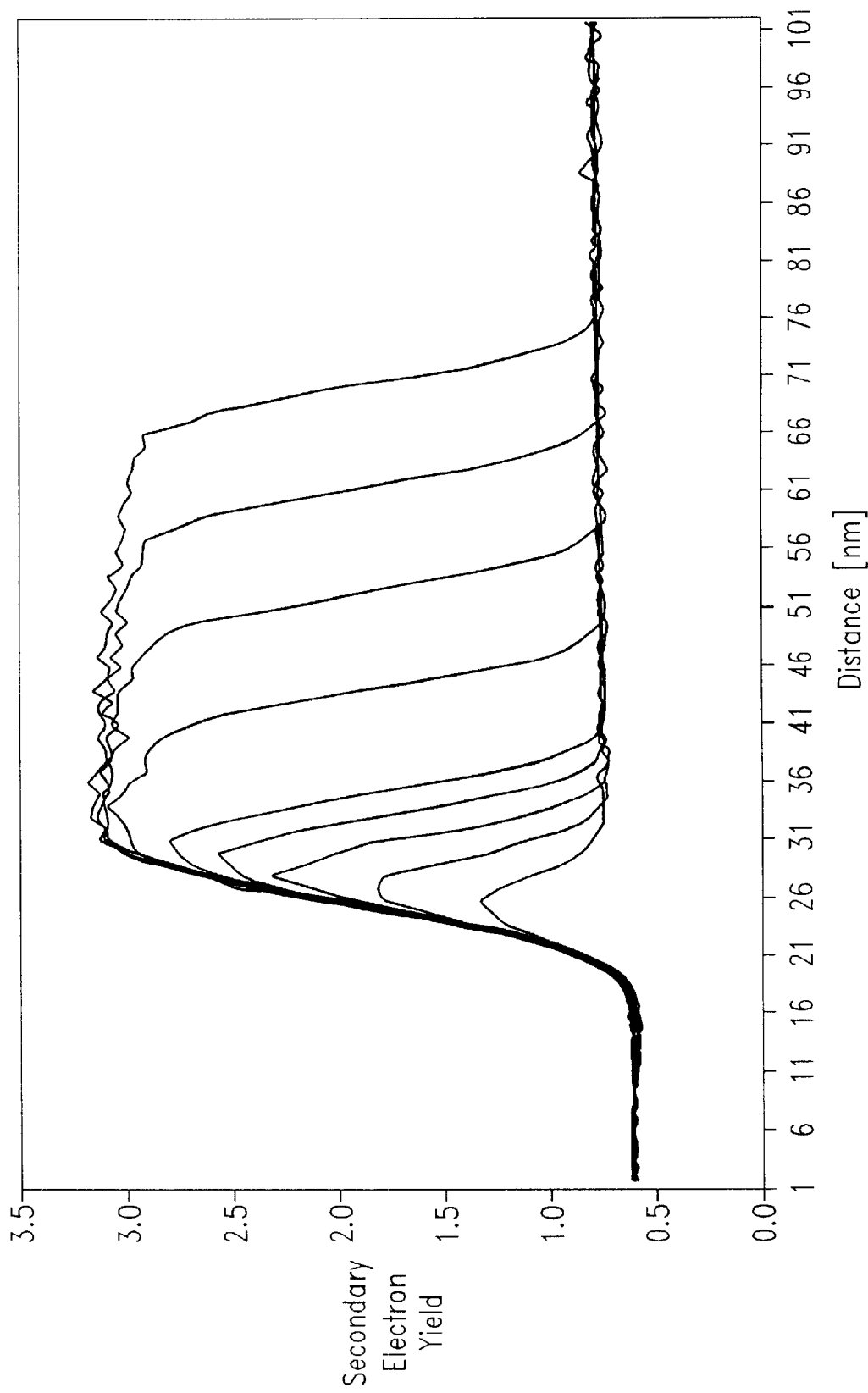
FIG. 7 is a graph showing an Edge waveform illustrating the effect of SEM-beam tilt angles on a single edge in greater detail.

FIG. 7 is a graph showing the effect of SEM-beam tilt angles on a single edge in greater detail. In FIG. 7, an Edge waveform is shown for various SEM-beam tilt angles on a single edge from zero degrees to 5 degrees (0°, 0.25°, 0.5°, 0.75°, 1°, 2°, 3°, 4°, and 5°).

Figure 8:
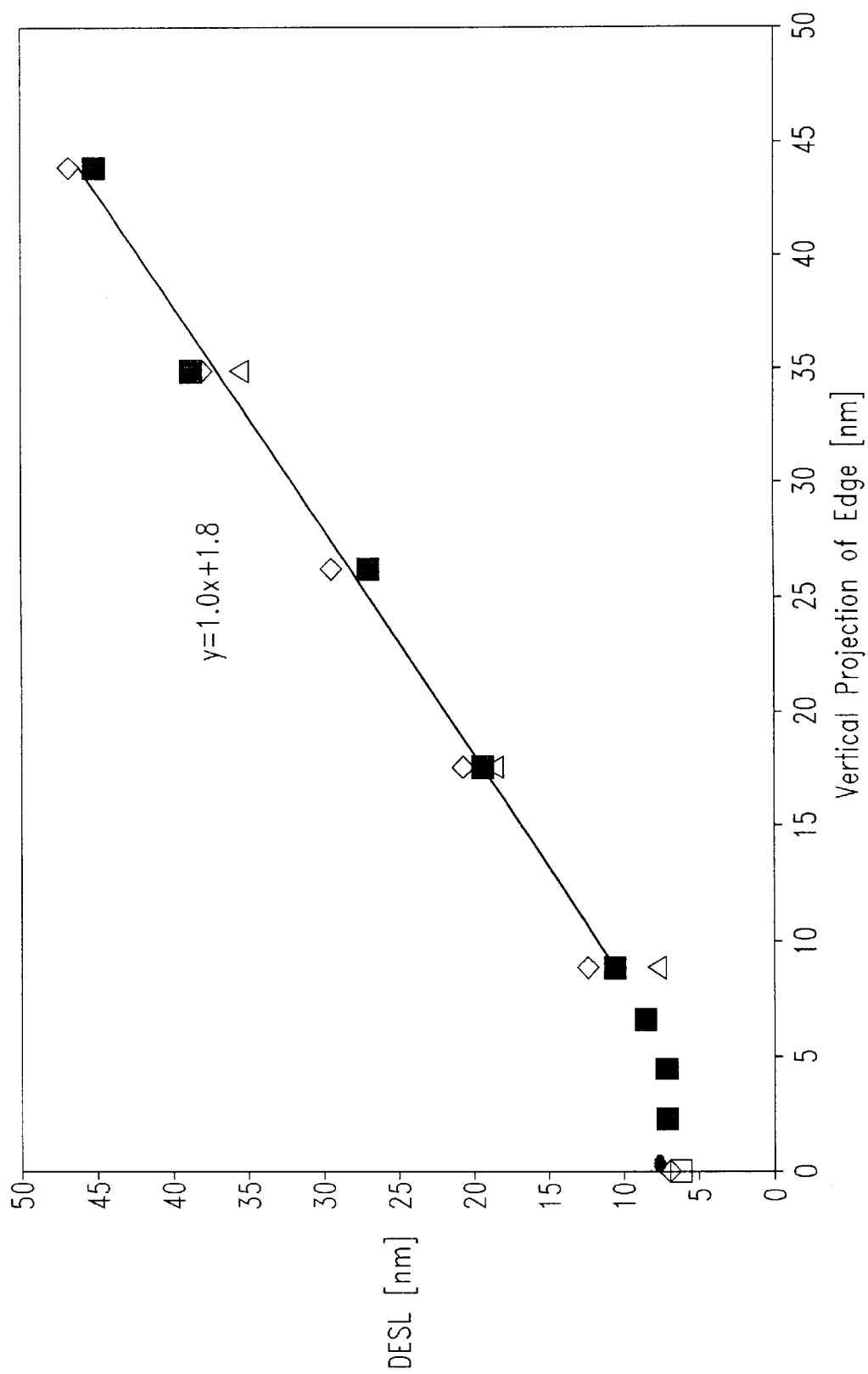
FIG. 8 is a plot of data showing the Distance between Extremal Slope Locations (DESL).

FIG. 8 is a plot of data representing the Distance between Extremal Slope Locations (DESL). That data was extracted from the data shown in FIG. 7 and plotted against the vertical projection of the edge, H tan θ. (Note: for small values of the angle θ this quantity is proportional to the angle.) Results from simulation for other beam and sample conditions are also shown. In this study, the structure height was 500 nm. The squares correspond to the data of FIG. 7 where the electron beam landing energy is 500 eV, the geometry is an isolated line, and the material of the structure is photoresist. Triangles represent data where the landing energy is 1000 eV, the geometry is an isolated line, and the material is photoresist. Circles represent data where the landing energy is 500 eV, the geometry is a nested line with equal line and space widths of 130 nm, and the material is photoresist. Diamonds represent data where the landing energy is 500 eV, the geometry is an isolated line, and the material is gold.

The linear fit to the data for edge projections greater than 10 nm in FIG. 8 is remarkable. With a slope close to unity and an intercept less than 2 nm in magnitude, the DESL is an excellent metric for the true projected edgewidth which can be expressed as H tan θ, where θ is the relative angle between the direction of the SEM-beam where it contacts the sample and the sidewall. A linear relationship with near unity slope is observed for a wide range of landing energy, beam spot size, and material properties provided the vertical projection of the edge is larger than the beam spot size. This criterion is easily determined by comparing a curve derived from a series of DESL values determined at different angles to the Apparent Beam Width (ABW) metric. While the unity slope generally holds true across beam and sample variations, the offset has some dependence on these properties. Therefore, the calibration exercise is generally needed to determine this offset.

Superior fits with subnanometer agreement to the data for all angles, beam and sample conditions considered are obtained by using the following formula: y The values of $K_0$ and K are beam and sample specific. Typically, $K_0$ has a value of approximately six (6) nm and K has a value of approximately two (2) nm.

A practical application of these concepts can be simplified in several ways. Typical sidewall angles of interest deviate from vertical by a few degrees or less. A SEM with capability of beam tilting will probably be restricted to SEM-beam deflection tilt angle of less than ten degrees (10°), since beyond that, nested structures and trenches with aspect ratios greater than five (5) cannot be fully viewed.

On the other hand, the height of the structure under investigation may not be well known. Some resist systems have the height of the developed resist dependent on the degrees of nesting of the structures. Consequently, a practical application of these ideas needs to determine structure height H as well as $\phi_0$.

Figure 9A:
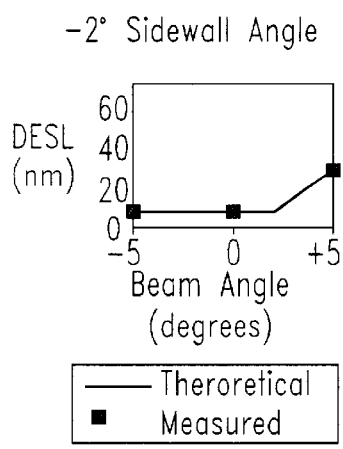
FIGS. 9A–9C are graphs showing the behavior of the DESL as a function of SEM-beam deflection tilt angle in degrees for the left edges of an isolated line for the range of SEM-beam deflection tilt angles measured for three sidewall angles.
Figure 9B:
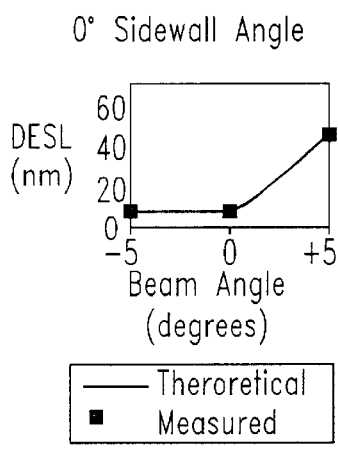
Figure 9C:
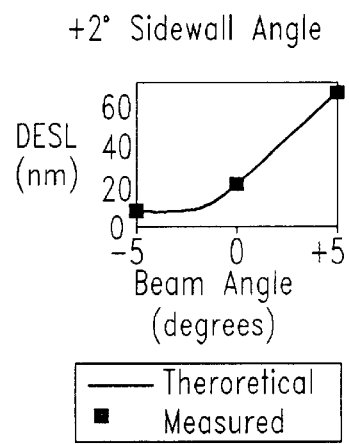

FIGS. 9A–9C are graphs showing the behavior of DESL values as a function of tilt angles in degrees of SEM-beam deflection for the left edges of isolated lines for the range of SEM-beam deflection tilt angles. Each graph shows a thin line representing a theoretical curve and a set of discrete measured tilt angles indicated by the boxes marked on the graphs which show that an ambiguity can sometimes arise in the interpretation of line scans if only three deflection tilt angles are used. The minus two degrees (−2°) sidewall angle could be interpreted as a zero degrees (0°) sidewall angle if the height of the resist structure is an unknown.

FIG. 9A shows the results of three determinations of DESL values for the left edge of the isolated line by measurement for a structure with a negative sidewall angle of two degrees. The measurements were done at minus five, zero, and plus five degrees (−5°, 0°, +5°). The sidewall is obscured and the same DESL value is determined. With only one measurement significantly greater than the others, there is not enough information available to determine the sidewall angle and the structure height H.

FIG. 9B is an example which shows the results of three determinations of DESL by measurement for a structure with vertical sidewall. This is similar to the case in FIG. 9A, with only one measurement significantly greater than the others there is not enough information to determine both the sidewall angle and the structure height.

FIG. 9C is a third example which shows the results of three determinations of DESL by measurement for a structure with a plus two degrees (+2°) sidewall angle. In this case with two measurements significantly greater than the minimum DESL value, the sidewall angle and structure height can be determined. FIG. 10B shows that, at the cost of employing two additional SEM-beam deflection tilt angles of −2.5 degrees and +2.5 degrees, ambiguity of FIG. 9B can be avoided.

Figure 10A:
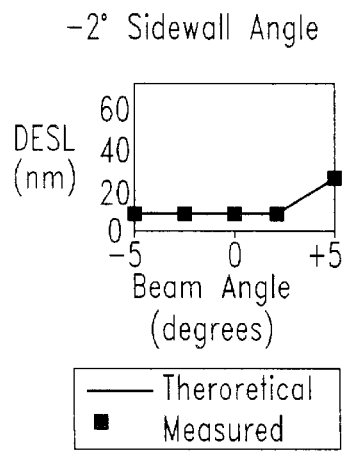
FIGS. 10A–10C show three graphs showing the edge DESL trends for the left edges of the isolated line of FIGS. 9A–9C as a function of an SEM-beam deflection tilt angle measured for five sidewall angles.
Figure 10B:
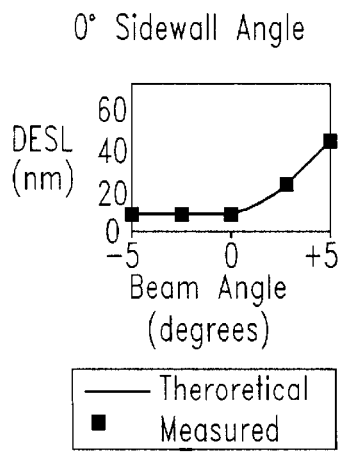
Figure 10C:
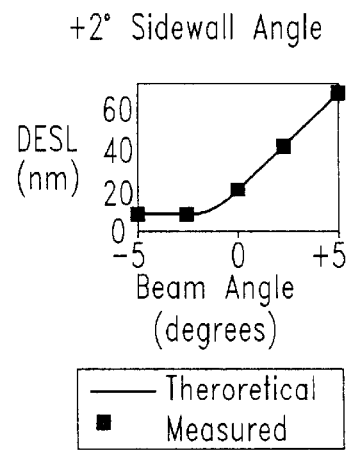

FIGS. 10A–10C show three graphs showing the edge DESL trends for the left edges of the isolated lines of FIGS. 9A–9C as a function of an SEM-beam deflection tilt angle for three sidewall angles.

FIG. 10A is a graph showing the results of five determinations of the DESL value trend for the left edge of the isolated lines of FIG. 9A by measurement for the structure with the negative sidewall angle of two degrees. The five SEM-beam deflection tilt angles are minus five, minus two and a half, zero, plus two and a half and plus five degrees (5°, −2.5°, 0°, +2.5°, +5°). Even though there are now five measured data points, this case has insufficient information to determine both the sidewall angle and the structure height. This case also illustrates another to insight gained from the modeling, namely, that the measurement at plus two and a half degrees (+2.5°) of tilt where, in principle, the edge is now exposed does not produce a significantly different result from the other cases of the obscured sidewall. This is because of the finite beam size and other resolution limiting effects.

In the case of FIG. 10B, the example of FIG. 9B now shows the results of the five determinations of DESL by measurement for the structure with the vertical sidewall. In this case with two measurements significantly greater than the minimum DESL value on the right side of the graph, the sidewall angle and structure height can be determined.

In the case of FIG. 10C, the example of FIG. 9C now shows the results of the five determinations of DESL by measurement for a structure with a plus two degrees (+2°) sidewall angle. In this case with three measurements significantly greater than the minimum DESL value, the sidewall angle and structure height can be determined. However, more data than necessary has been taken since there was sufficient data as shown in FIG. 9C.

The preferred embodiment comprises hardware capable of quickly acquiring SEM waveforms of a semiconductor structure at multiple tilt (beam or stage) angles. Because of uncertainty in structure height and possible left-right asymmetry, generally five (5°) tilt angles are required. From these waveforms, the Distance between Extremal Slope Locations (DESL) is determined for each edge. The data points are fitted to a specific functional form (see the above equation) thereby determining structure height and sidewall angles. This information can be used to correct the top/down zero degrees (0°)tilt angle line width measurement for negative sidewall angle, if necessary.

Figure 11A:
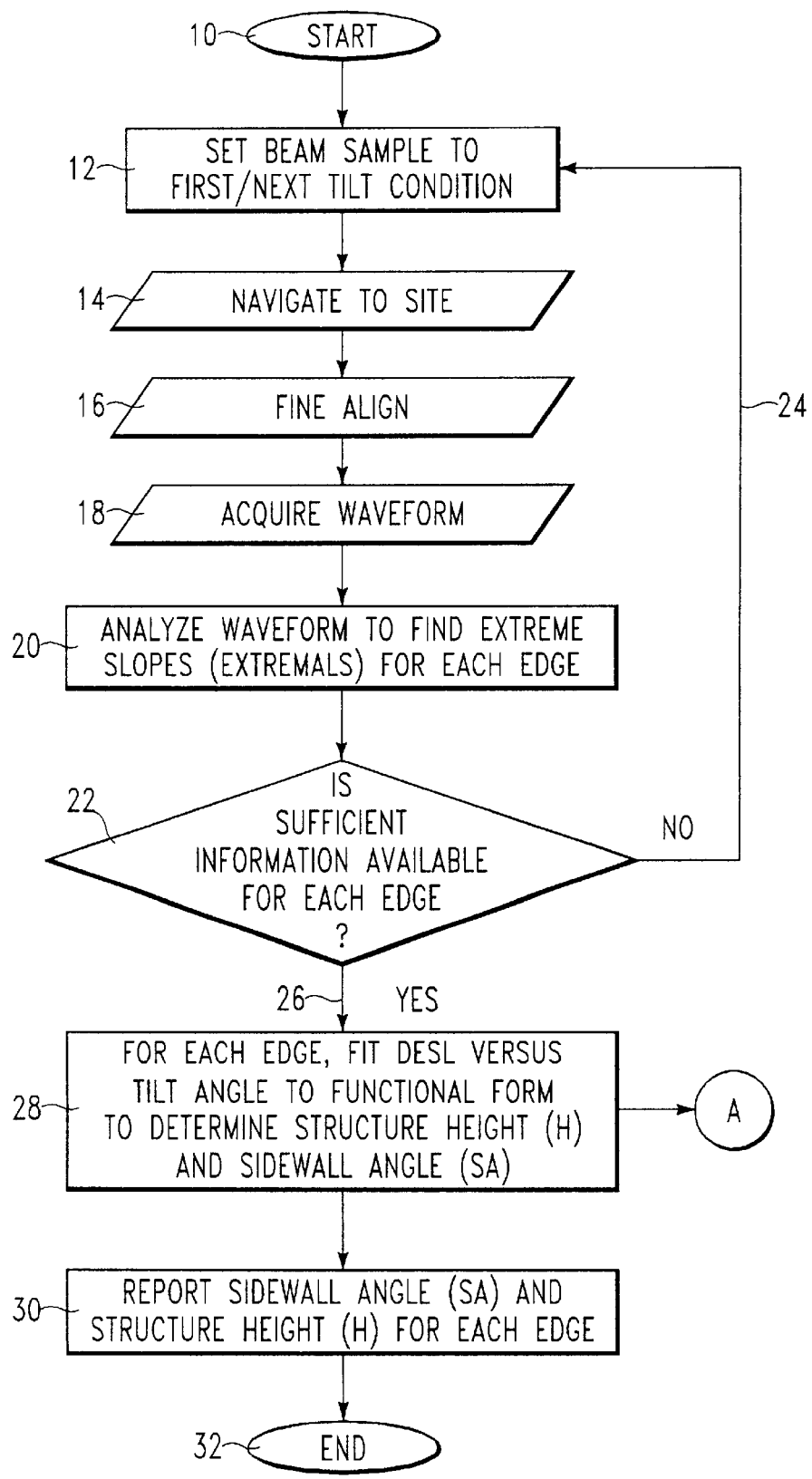
FIG. 11A is a flow chart of the program for performing the tilted SEM-beam scanning method in accordance with this invention.

FIG. 11A shows a flow chart of the program for performing the tilted SEM-beam scanning method of this invention. In step 10, the program begins, followed by step 12 which is to set the beam sample to the first/next tilt condition.

In step 14, the system navigates the SEM to the sample site.

In step 16, the system performs a fine alignment step.

In step 18, the system acquires the waveform as in FIG. 1A.

In step 20, the system analyzes the waveform to find extremal slopes for each edge of the sample bump or other feature. This results in a DESL value at given tilt angle for each edge of interest.

In step 22, the system tests whether there is sufficient information available for each edge, i.e. a sufficient number of the DESL values are greater than the threshold value.

If NO, the system branches along line 24 back to step 12 and repeats the above sequence of steps. If YES, the system proceeds along line 26 (YES) to step 28.

In step 28, for each edge, the system fits DESL versus tilt angle to functional form to determine structure height (H) and sidewall angle.

The algorithm used in step 28 is to determine the DESL information as a function of tilt angle is as follows. Provided all the DESL values being used for one edge (two or more) are greater than the threshold value, then the DESL values [nm] versus tilt angle [radians] is fitted to a straight line. The important properties of the straight line are the slope and the Y-axis intercept. Because the cases of practical interest have the sidewall angle and the beam tilt angles small (less than 10 degrees), $\tan \theta = \theta$ is a good approximation. If applied to a situation with larger angles, the modification of the method is straightforward. In the small angle case, the slope determined from the straight-line-fit is the structure height in nanometers. The Y-axis intercept determined from the linear regression determines the sidewall angle by the following formula:

$$\text{sidewall angle} = \frac{(\text{Y-axis intercept}) - K}{\text{Height}}$$

In a situation where one of the DESL values to be used is close to the value of the sum of $K_0+K$ determined during calibration, then a more accurate, non-linear analysis is necessary. The DESL and tilt angle values will be fit to the following functional form with the structure height and sidewall angle being the fitting parameters:

$$DESL = \sqrt{[H*\tan(\phi_0 + \varphi_e)]^2 + K_0^2} + K$$

where $H$ = structure height, $\phi_0$ = sidewall angle deviation from vertical, $\varphi_e$ = tilt of the SEM-beam, $DESL$ = Distance between Extermal Slope Locations $K_0$ = constant determined during calibration $K$ = constant determined during calibration In step 30 of FIG. 11A, the system reports the sidewall angle SA and the structure height H for each edge of the structure under test.

Referring to the case of FIG. 9B, after completion of three loops between the step 12 and step 22 of FIG. 11 A, three determinations of DESL at tilt angles of −5, 0, and 5 degrees have been performed but only one of the DESL values is above the minimum threshold. Another return to step 12 is indicated. Since the one DESL value that is above threshold was at 5 degrees, ideally a new tilt angle even greater should be tried. However, perhaps because of practical limitations in the equipment this is not possible. Another strategy is to choose a tilt angle between this successful result at 5 degrees and the previous unsuccessful one at 0 degrees. In FIG. 10B, such a value at 2.5 degrees is plotted and it succeeds in being above threshold. This illustrates strategies to try when insufficient DESL information has been gathered.

FIG. 9A illustrates another possible situation. Again since only one DESL value is above threshold after three loops between step 12 and step 23 of FIG. 11, another return to step 12 is indicated. However, if a greater tilt angle than 5 degrees is not possible, then try a tilt angle between the successful one (5 degrees) and the one previous to that (0). The value of 2.5 degrees splits the difference and the DESL result is shown in FIG 10A. Unfortunately, this too has failed to produce a DESL value above threshold. A possible strategy at this point is to split the difference again between the angle of the successful DESL (5 degrees) result and this last effort (2.5 degrees). This case (3.75 degrees) is not shown but a proper reading of the theory as to the curve in these figures shows that the resulting DESL would be above threshold and thus complete the data taking part of the flow chart.

Critecal Dimension of Structure with Negative Sidewall Angle

As stated above, in some cases the prior art is capable of measuring the Critical Dimension CD where a structure has two exposed sidewalls which are not obscured by overhanging edges. However, in a case in which either sidewall SW of the feature being examined has a base which is obscured because of a Negative Sidewall Angle, where the Critical Dimension comprises the Base Width BW or the Maximum Structure Width MSW, in accordance with this invention a correction of the data available in accordance the prior art is made which uses all the structural information collected in accordance with this invention.

Figure 11B:
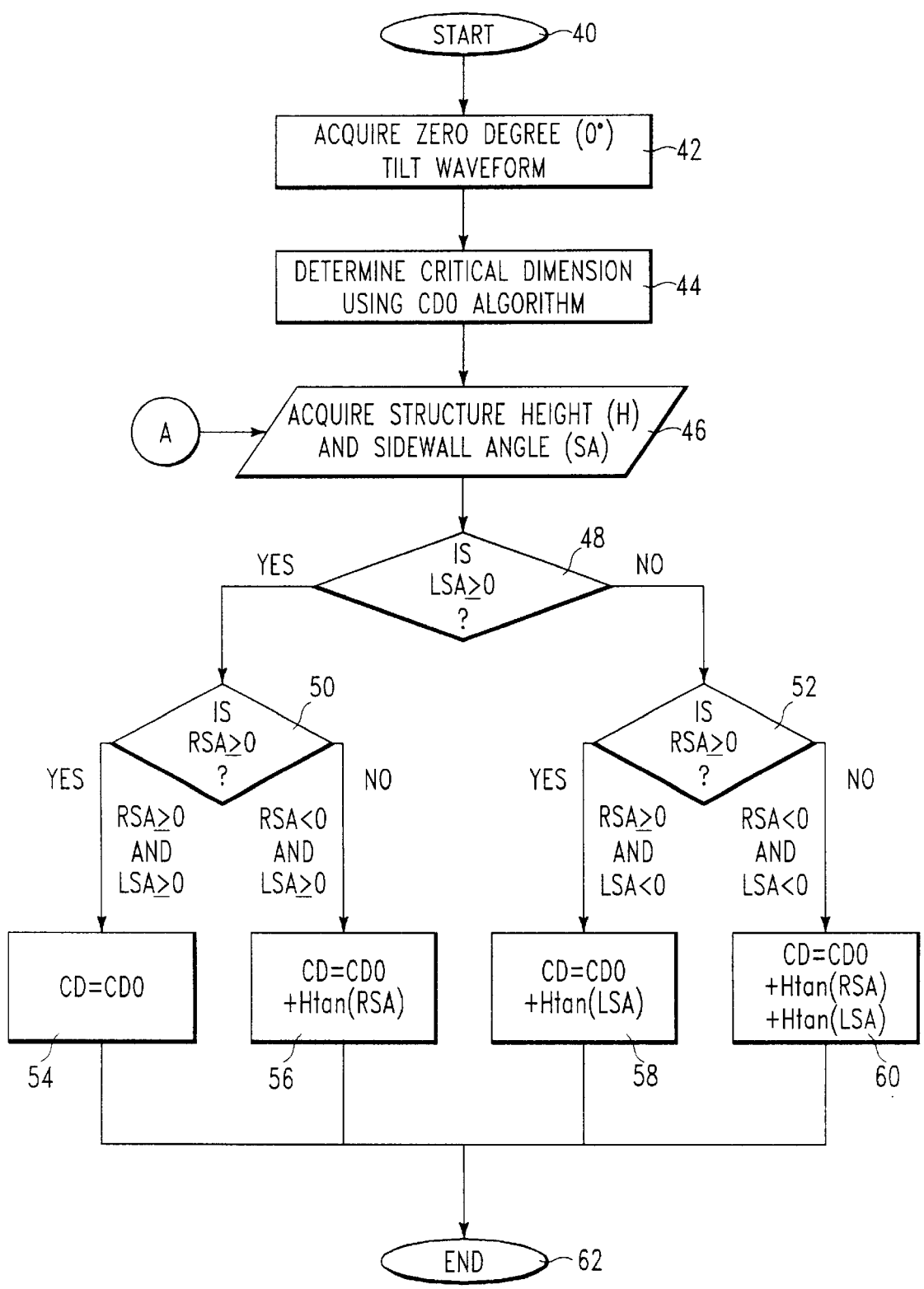
FIG. 11B is a flow chart of a program for providing a correction that must be added to determine the edge base location, which is H tan(SA) where H is the structure height and SA is the sidewall angle assuming that the prior art algorithm in the case of a negative sidewall angle is actually finding the location of the edge only at the top of the structure.

Referring to FIG. 11B, assuming that the prior art algorithm in the case of a negative sidewall angle is actually finding the location of the edge only at the top of the structure, then there is a correction that must be added to determine the edge base location, which is H tan(SA) where H is the structure height and SA is the sidewall angle. This correction should be applied to both the left and right edges of the structure, if both have negative sidewall angles NSA. So, in general, if CD stands for the Critical Dimension to be reported and CDO stands for the result from the prior art algorithm, then perform the calculations as follows:

| | |
|---|---|
| CD = CD0 | if RSA ≧ 0 and LSA ≧ 0 |
| CD = CD0 + Htan(RSA) | if RSA < 0 and LSA ≧ 0 |
| CD = CD0 + Htan(LSA) | if RSA ≧ 0 and LSA < 0 |
| CD = CD0 + Htan(RSA) + Htan(LSA) | if RSA < 0 and LSA < 0. |

Figure 11C:
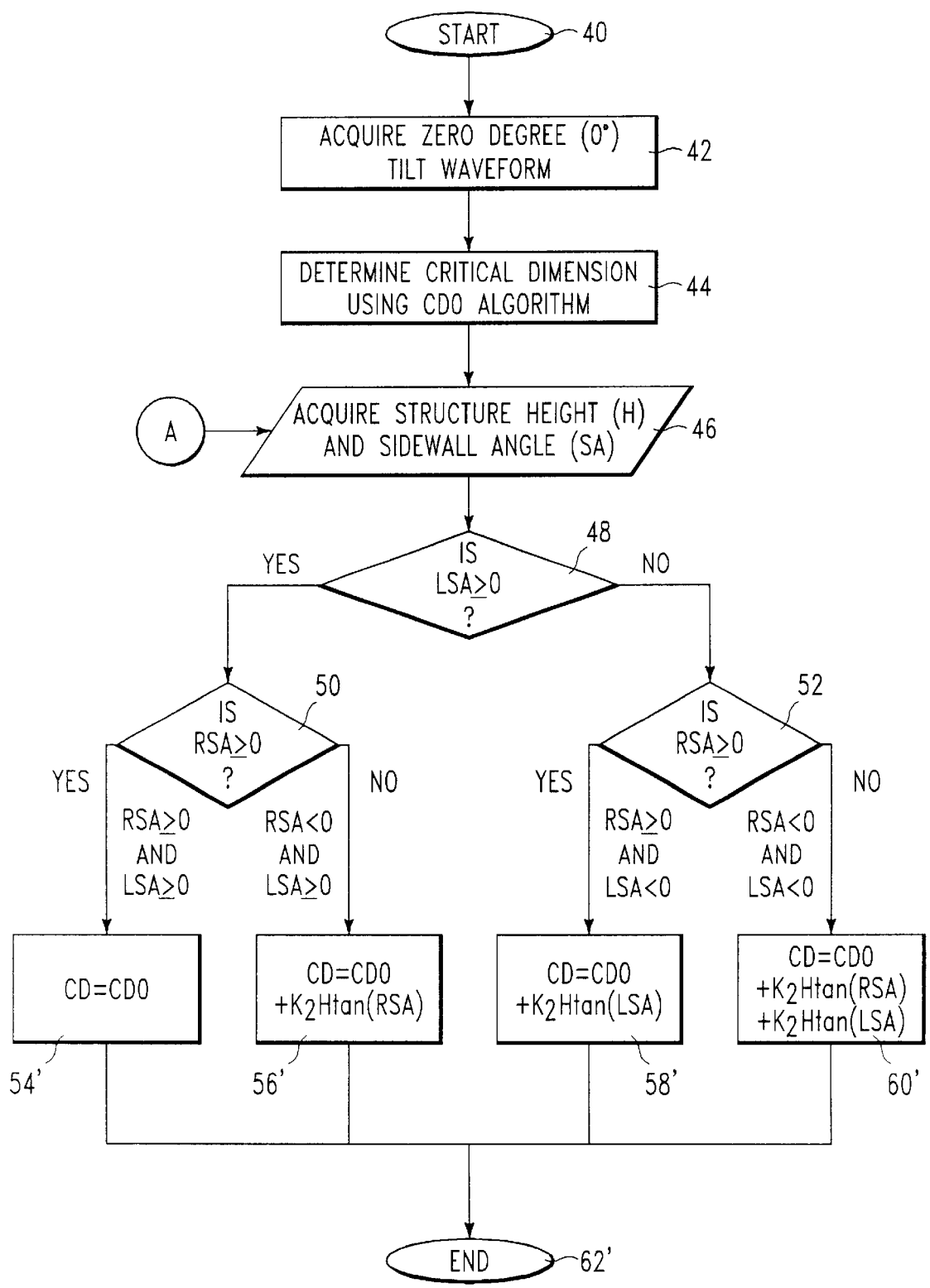
FIG. 11C is a flow chart of a program which is an alternative to FIG. 11B that provides the flexibility needed to handle multiple prior art algorithms and multiple definitions of the critical dimension can be achieved by allowing the user to choose an appropriate value for a constant K2.

The flexibility needed to handle multiple prior art algorithms and multiple definitions of the critical dimension can be achieved by allowing the user to choose an appropriate value for the constant $K_2$ in the following modified version as shown in FIG. 11C, the calculation is as follows:

| | |
|---|---|
| CD = CD0 | if RSA ≧ 0 and LSA ≧ 0 |
| CD = CD0 + $K_2$Htan(RSA) | if RSA < 0 and LSA ≧ 0 |
| CD = CD0 + $K_2$Htan(LSA) | if RSA ≧ 0 and LSA < 0 |
| CD = CD0 + $K_2$Htan(RSA) + $K_2$Htan(LSA) | if RSA < 0 and LSA < 0 |

While the above decision making and calculation could be made by a host computer once all the information has been sent from the CDSEM, it is preferred for real time reporting that the CDSEM computer actually do this processing.

EXAMPLE

Consider a system where during calibration it was determined that $K_0$=6 nm, K=2 nm and the threshold was chosen to be 16 nm. The system first acquires a waveform with a vertical electron beam (0 degrees of tilt) and the DESL determined for an edge of interest is 8 nm. Next the system sets up a tilted beam of 2 degrees and determines for that condition the DESL is 8 nm. Neither DESL value determined so far is above the threshold, so the system sets up a new tilt of 4 degrees; the resulting DESL is determined to be 20 nm. There is now one DESL value above the threshold but the system needs at least two values above the threshold, so a new tilt angle is set: 6 degrees. The resulting DESL is 35 nm. There are now two DESL values above threshold and the system can now proceed to determine the structure height and sidewall angle. The data collected are listed in the following table:

| Angle [Deg] | Angle [Radians] | DESL [nm] |
|---|---|---|
| 0 | 0.000 | 8 |
| 2 | 0.035 | 8 |
| 4 | 0.070 | 20 |
| 6 | 0.105 | 35 |

Figure 12:
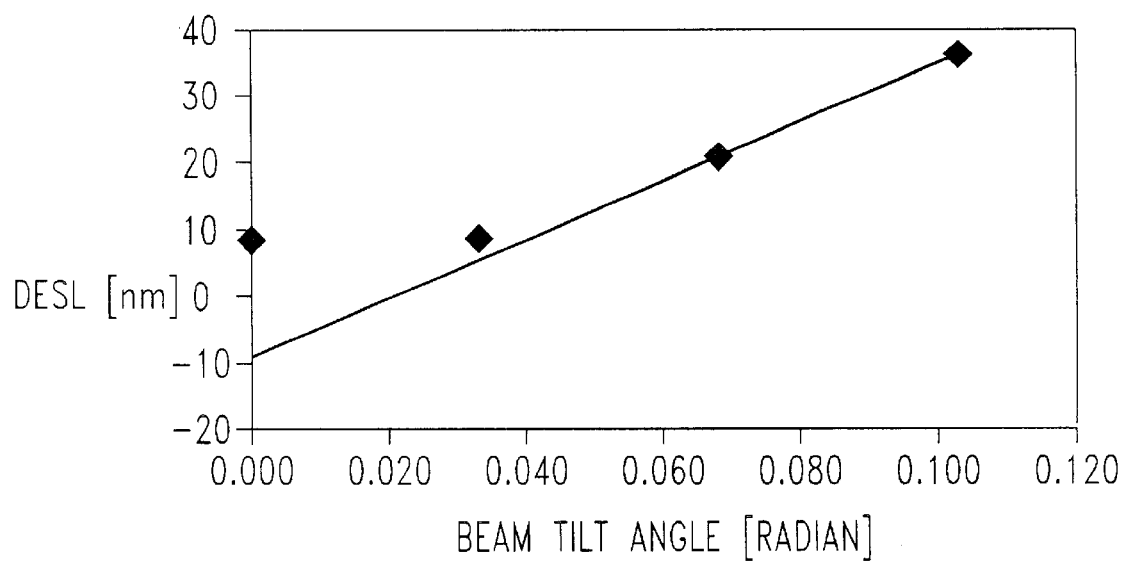
FIG. 12 is a graph of DESL vs. Beam Tilt Angle for an example which is illustrative of this invention.

These data are plotted in the graph shown in FIG. 12.

The two DESL values above threshold determine a straight line as shown in FIG. 12. The slope of this line is 430 nm. This is the height H of the structure. The y-intercept is −10 nm. Using the formula:

$$\text{sidewall angle} = \frac{(\text{Y-axis intercept}) - K}{\text{Height}} = \frac{(-10 \text{ nm}) - (2 \text{ nm})}{(430 \text{ nm})} = -0.28 \text{ radians}$$

When expressed in degrees this is −1.6 degrees; the sidewall is recursive with a negative sidewall angle of −1.6 degrees.

While this invention has been described in terms of the above specific embodiment(s), those skilled in the art will recognize that the invention can be practiced with modifications within the spirit and scope of the appended claims, i.e. that change can be made in form and detail, without departing from the spirit and scope of the invention. Accordingly, all such changes come within the purview of the present invention and the invention encompasses the subject matter of the claims which follow.

Having thus described the invention, what is claimed as new and desirable to be secured by Letters Patent is as follows:

1. A method for extracting structural information on a workpiece by having a scanning electron microscope (SEM) scan the workpiece to acquire waveform information at a plurality of tilt angles, wherein the process of extracting the structural information extends beyond the resolution of the SEM, the method comprising the steps of:

(a) setting an SEM beam to a first/next tilt angle;

(b) scanning across a region of the workpiece at the tilt angle to acquire a waveform;

(c) analyzing the waveform to extract a Distance between Extremal Slope Locations (DESL) value for each edge of interest;

(d) determining whether there are two acceptable DESL values for each structural edge by comparing each DESL value to a DESL threshold value; wherein, if there are at least two of said DESL values that are greater than said DESL threshold value, then sufficient information has been obtained, and else, returning to step a), and (e) determining the height and the sidewall angle of the structure on the workpiece, wherein when both of said DESL values are greater than at least 1.5 times the DESL threshold value, then a geometrical analysis extracts the height and sidewall angle of the structure on the workpiece, and when either of said two DESL values is smaller than at least 1.5 times said DESL threshold value, then the geometrical analysis is modified to include limitations in the resolution of the SEM.

2. The method of claim 1, wherein said DESL threshold value is determined by a calibration process.

3. The method of claim 1, wherein added properties of each edge of interest are extracted from said waveform at various tilt angles.

4. The method of claim 3, wherein said added properties are three dimensional properties.

5. A method for making Scanning Electron Microscope (SEM) scans of a workpiece comprising:

(a) setting an SEM beam to a first/next deflection tilt angle, (b) scanning across a region of the workpiece at the deflection tilt angle to acquire a waveform, (c) analyzing a waveform to determine a DESL value for each edge of interest, (d) determining whether there is sufficient information for each structural edge and if NO returning to step (a) and if YES proceeding to step (e), (e) determining height (H) and sidewall angle values for each structural edge, and (f) determining height (H) and sidewall angle for each structural edge; and performing the calculations as follows:

CD=CDO if RSA>0 and LSA>$_{13}$ 0

CD=CDO+H tan(RSA) if RSA<0 and LSA>$_{13}$ 0

CD=CDO+H tan(LSA) if RSA>$_{13}$ 0 and LSA<0

CD=CDO+H tan(RSA)+H tan(LSA) if RSA<0 and LSA<0

6. The method of claim 5 including fitting the DESL versus tilt angle to functional form to determine structure height (H) and sidewall angle.

7. The method of claim 5 including performing the calculations as follows:

| | |
|---|---|
| CD = CD0 | if RSA ≧ 0 and LSA ≧ 0 |
| CD = CD0 + K$_2$Htan(RSA) | if RSA < 0 and LSA ≧ 0 |
| CD = CD0 + K$_2$Htan(LSA) | if RSA ≧ 0 and LSA < 0 |
| CD = CD0 + K$_2$Htan(RSA) + K$_2$Htan(LSA) | if RSA < 0 and LSA < 0. |

8. The method of claim 5 further including the step of performing the following calculation $$\text{Sidewall angle} = \frac{(\text{Y-axis intercept}) - K}{\text{height}}$$

wherein height=slope, and the slope and the Y-axis intercept represent a straight line fit to a plot of DESL values versus the tilt angle.

9. A method for processing edge and sidewall data comprising:

fitting DESL (Distance between Extremal Slope Locations) to the data for all angles, beam and sample conditions by using the formula as follows:

10. An apparatus for extracting structural information on a workpiece for having a scanning electron microscope (SEM) scan the workpiece to acquire waveform information at a plurality of tilt angles, wherein the process of extracting the structural information extends beyond the resolution of the SEM, the apparatus comprising (a) means for setting an SEM beam to a first/next tilt angle, (b) means for scanning across a region of the workpiece at the tilt angle to acquire a waveform;

(c) means for analyzing the waveform to extract a Distance between Extremal Slope Locations (DESL) value for each edge of interest;

(d) means for determining whether there are two acceptable DESL values for each structural edge by comparing each DESL value to a DESL threshold value; wherein, if there are at least two of said DESL values that are greater than said DESL threshold value, then sufficient information has been obtained, and else, returning to step a), and (e) means for determining the height and the sidewall angle of the structure on the workpiece, wherein when both of said DESL values are greater than at least 1.5 times the DESL threshold value, then a geometrical analysis extracts the height and sidewall angle of the structure on the workpiece, and when either of said two DESL values is smaller than at least 15 times said DESL threshold value, then the geometrical analysis is modified to include limitations in the resolution of the SEM.

11. The apparatus of claim 10, wherein said DESL threshold value is determined by a calibration process.

12. The apparatus of claim 10, wherein added properties of each edge of interest are extracted from said waveform at various tilt angles.

13. The apparatus of claim 12, wherein added properties are three-dimensional properties.

14. The apparatus of claim 11 including means for performing the calculations as follows:

| | |
|---|---|
| CD = CD0 | if RSA $\geq$ 0 and LSA $\geq$ 0 |
| CD = CD0 + Htan(RSA) | if RSA < 0 and LSA $\geq$ 0 |
| CD = CD0 + Htan(LSA) | if RSA $\geq$ 0 and LSA < 0 |
| CD = CD0 + Htan(RSA) + Htan(LSA) | if RSA < 0 and LSA < 0. |

15. The apparatus of claim 11 including means for performing the calculations as follows:

| | |
|---|---|
| CD = CD0 | if RSA $\geq$ 0 and LSA $\geq$ 0 |
| CD = CD0 + $K_2$Htan(RSA) | if RSA < 0 and LSA > 0 |
| CD = CD0 + $K_2$Htan(LSA) | if RSA > 0 and LSA < 0 |
| CD = CD0 + $K_2$Htan(RSA) + $K_2$Htan(LSA) | if RSA < 0 and LSA < 0. |

16. The apparatus of claim 11 including means for performing the calculations as follows:

$$\text{sidewall angle} = \frac{(\text{Y-axis intercept}) - K}{\text{Height}}$$

17. Apparatus for processing edge and sidewall data comprising:

means for fitting DESL (Distance between Extremal Slope Locations) to the data for all angles, beam and sample conditions by using the formula as follows:

* * * * *